United States Patent [19]

Dean et al.

[11] Patent Number: 5,510,347
[45] Date of Patent: Apr. 23, 1996

[54] THIENOTHIADIAZINE SULFONAMIDES USEFUL AS CARBONIC ANHYDRASE INHIBITORS

[75] Inventors: Thomas R. Dean, Weatherford, Tex.; Abdelmoula Namil, Cappelle en Pevéle, France

[73] Assignee: Alcon Laboratories, Inc., Fort Worth, Tex.

[21] Appl. No.: 303,991

[22] Filed: Sep. 9, 1994

[51] Int. Cl.$^6$ ........................ C07D 285/16; A61K 31/54
[52] U.S. Cl. ............................................. 514/222.8; 544/10
[58] Field of Search ............................ 514/222.8; 544/10

[56] References Cited

U.S. PATENT DOCUMENTS

| | | | |
|---|---|---|---|
| 4,619,939 | 10/1986 | Maren | 514/363 |
| 4,797,413 | 1/1989 | Baldwin et al. | 514/432 |
| 5,153,192 | 10/1992 | Dean et al. | 514/226.5 |
| 5,240,923 | 8/1993 | Dean et al. | 514/226.5 |
| 5,308,863 | 5/1994 | Baldwin et al. | 514/431 |

FOREIGN PATENT DOCUMENTS 452151  10/1991  European Pat. Off. .

*Primary Examiner*—John M. Ford
*Attorney, Agent, or Firm*—Sally Yeager

[57] ABSTRACT

New thienothiadiazine sulfonamides useful as carbonic anhydrase inhibitors are disclosed. Methods for using the compounds to control IOP are also disclosed.

6 Claims, No Drawings

THIENOTHIADIAZINE SULFONAMIDES USEFUL AS CARBONIC ANHYDRASE INHIBITORS

FIELD OF THE INVENTION

The present invention relates to new thienothiadiazine sulfonamides useful in lowering and controlling intraocular pressure.

BACKGROUND OF THE INVENTION

Glaucoma is a disease of the eye which is characterized by a progressive loss of visual field due to irreversible damage to the optic nerve. If untreated, this condition can result in blindness. This loss of visual field, in one form of primary open angle glaucoma, that is, chronic primary open angle glaucoma, hereinafter POAG, is associated with a sustained increase in the intraocular pressure (IOP) of the diseased eye. In addition, elevated intraocular pressure without visual field loss, or ocular hypertension, can be indicative of the early stages of POAG.

There are a number of therapies that target reducing the elevated IOP associated with ocular hypertension or POAG. The most common feature the topical administration of a beta adrenergic antagonist (beta-blocker) or a muscarinic agonist. These treatments, while effective in lowering IOP, can also produce significant undesirable side effects.

Another less common treatment for ocular hypertension or POAG is the systemic administration of carbonic anhydrase inhibitors; however, this therapy can also bring about unwanted side effects, such as nausea, dyspepsia, fatigue, and metabolic acidosis. Topical administration of carbonic anhydrase inhibitors can be used to control IOP with a reduced risk of encountering the aforementioned systemic side effects. U.S. Pat. Nos. 5,153,192; 5,240,923; 4,797,413; 5,308,863; and EPO 91/452,151A1 disclose topically dosed sulfonamides which lower IOP by inhibiting carbonic anhydrase.

SUMMARY OF THE INVENTION

The present invention is directed to new thienothiadiazine sulfonamides which can be used to lower and control IOP. The compounds are formulated in pharmaceutical compositions for delivery.

The invention is also directed to methods for treating ocular hypertension and POAG by lowering and controlling IOP by the administration of the thienothiadiazine sulfonamides of the present invention. The compounds can be administered systemically and/or topically to the eye.

DETAILED DESCRIPTION OF THE INVENTION

The thienothiadiazine sulfonamides of the present invention have the following structure.

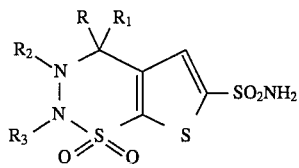

or a pharmaceutically acceptable salt thereof wherein:

R is H or $C_{1-2}$ alkyl;

$R_1$ is H; $C_{1-6}$ alkyl unsubstituted or substituted optionally with OH, $C_{1-4}$ alkoxy, $NR_4R_5$, $OC(=O)R_6$ or $C(=O)R_6$;

$R_2$ is H; $C_{1-6}$ alkyl; $C_{2-4}$ alkyl substituted with OH, $NR_4R_5$, halogen, $C_{1-4}$ alkoxy, $C_{2-4}$ alkoxy$C_{1-4}$ alkoxy, $OC(=O)R_6$, $S(=O)_mR_7$, or $C(=O)R_6$; $C(=O)R_6$;

$R_3$ is H; $C_{1-8}$ alkyl; $C_{1-8}$ alkyl substituted with OH, $NR_4R_5$, halogen, $C_{1-4}$ alkoxy, $C_{2-4}$ alkoxy$C_{1-4}$ alkoxy, $OC(=O)R_6$, $S(=O)_mR_7$, or $C(=O)R_6$; $C_{1-7}$ alkenyl unsubstituted or substituted optionally with OH, $NR_4R_5$, or $C_{1-4}$ alkoxy; $C_{3-7}$ alkynyl unsubstituted or substituted optionally with OH, $NR_4R_5$, or $C_{1-4}$ alkoxy; $C_{0-3}$ alkyl substituted with $R_7$ which can be unsubstituted or substituted optionally with $C_{1-3}$ alkyl, $C_{1-3}$ haloalkyl, OH, $(CH_2)_nNR_4R_5$, halogen, $C_{1-4}$ alkoxy, $C_{1-4}$ haloalkoxy, $OC(=O)R_6$, $C(=O)R_6$, $S(=O)_mR_8$ or $SO_2NR_4R_5$, wherein m is 0–2 and n is 0–2;

$R_4$ and $R_5$ are the same or different and are H; $C_{1-8}$ alkyl; $C_{2-4}$ alkyl substituted optionally with OH, halogen, $C_{1-4}$ alkoxy or $C(=O)R_6$; OH; $C_{1-4}$ alkoxy; $C_{2-4}$ alkoxy substituted optionally with OH, halogen, $C_{1-4}$ alkoxy or $C(=O)R_6$; or $R_4$ and $R_5$ can be joined to form a ring of 5 or 6 atoms selected from O, S, C or N which can be unsubstituted or substituted optionally on carbon with OH, (=O), halogen, $C_{1-4}$ alkoxy, $C(=O)R_6$, $C_{1-6}$ alkyl, $C_{1-6}$ alkyl substituted optionally with OH, halogen, $C_{1-4}$ alkoxy, $C(=O))R_6$ or on nitrogen with $C_{1-4}$ alkoxy, $C(=O)R_6$, $S(=O)_mR_8$, $C_{1-6}$ alkyl or $C_{2-6}$ alkyl substituted optionally with OH, halogen, $C_{1-4}$ alkoxy, $C(=O)R_6$ or on sulfur by $(=O)_m$, wherein m is 0–2.

$R_6$ is $C_{1-8}$ alkyl; $C_{1-4}$ alkyl substituted optionally with OH, $NR_4R_5$, halogen, $C_{1-4}$ alkoxy or $C(=O))R_9$; $C_{1-4}$ alkoxy; $C_{2-4}$ alkoxy substituted optionally with OH, $NR_4R_5$, halogen or $C_{1-4}$ alkoxy; or $NR_4R_5$.

$R_7$ is a monocyclic ring system of 5 or 6 atoms composed of C, N, O and/or S, such as benzene, furan, thiophene, pyrrole, pyrazole, imidazole, triazole, tetrazole, oxazole, isoxazole, isothiazole, thiazole, thiadiazole, pyridine pyrimidine, pyridazine, and pyrazine.

$R_8$ is $C_{1-4}$ alkyl; $C_{2-4}$ alkyl substituted optionally with OH, $NR_4R_5$, $C_{1-4}$ alkoxy or $C(=O)R_6$; $R_7$ which can be unsubstituted or substituted optionally with OH, $(CH_2)_nNR_4R_5$, halogen, $C_{1-4}$ alkoxy, $C_{1-4}$ haloalkoxy, $C(=O)R_6$, $S(=O)_mC_{1-4}$ alkyl or $SO_2NR_4R_5$; wherein m is 0–2 and n is 0–2; and $R_9$ is $C_{1-4}$ alkyl; $C_{1-4}$ alkoxy; amino, $C_{1-3}$ alkylamino, of di-$C_{1-3}$ alkylamino.

In the above definitions, the total number of carbon atoms in a substituent group is indicated by the $C_{i-j}$ prefix where i and j are numbers from 1 to 8 for example. This $C_{i-j}$ definition includes both the straight and branched chain isomers. For example, $C_{1-4}$ alkyl would designate methyl through the butyl isomers and includes cyclopropylmethyl; and $C_{1-3}$ alkoxy would designate methoxy through the butoxy isomers.

The term "halogen," either alone or in compound words such as "haloalkyl," means fluorine, chlorine, bromine or iodine. Further, when used in compound words such as "haloalkyl," said alkyl may be partially or fully substituted with halogen atoms, which may be the same or different.

The compounds are advantageous due to their ease of synthesis with respect to the 4-unsubstituted compounds as they do not possess chiral centers within the bicyclic nucleus. There are chiral compounds in the compounds, 1, and this invention includes all enantiomers, diastereomers, and mixtures thereof.

Compounds, 1, can be prepared using methods and modifications thereof described below in Schemes 1 and 2. The choice of which method to use depends on the type of the R, $R_1$, $R_2$ and $R_3$ substituents and their compatibility with the reaction conditions used in the scheme. One skilled in the art is well equipped to make these selections.

One of the more direct routes to 1 is via the alkylation of compounds 2 (Scheme 1a). This method takes advantage of the fact that alkylations of the anion derived from 2 generally occur selectively at the N-3 position. Intermediates of 3 can be converted directly to 1a using Scheme 1b. Additionally, the secondary sulfonamide groups in 1a can be selectively alkylated to furnish 1b with more elaborate $R_3$ substituents (Scheme 1c).

Scheme 1a:

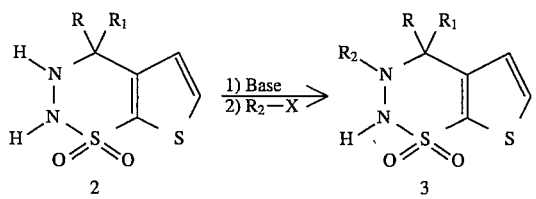

Scheme 1b:

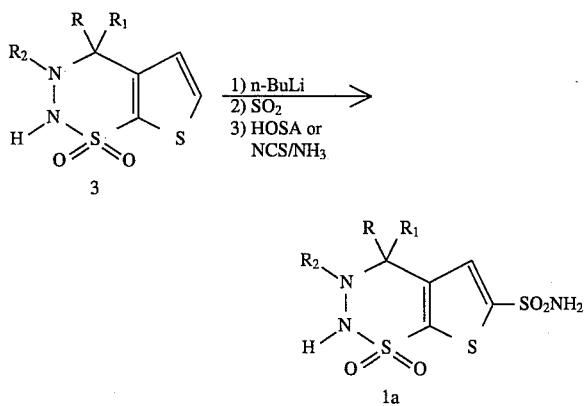

Scheme 1c:

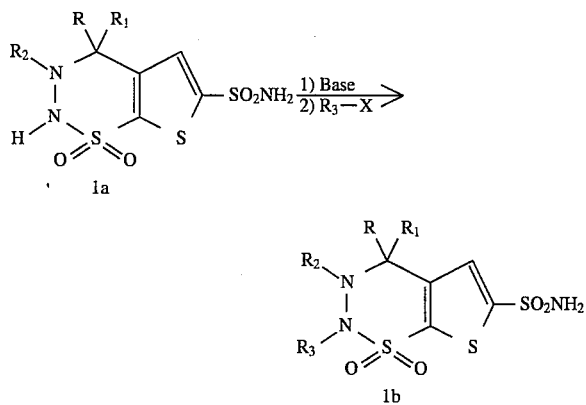

Compounds, 2, are dissolved or suspended in a polar aprotic solvent, such as N, N-Dimethylformamide (DMF) or dimethylsulfoxide (DMSO), containing an excess of base, such as sodium hydride (NaH), potassium tert-butoxide (tBuOK), or sodium carbonate ($Na_2CO_3$) (Scheme 1a). The electrophile ($R_2$—X, wherein $R_2$ is $C_{1-6}$ alkyl or $C_{2-4}$ alkyl substituted as previously defined) is added usually in a moderate excess and the mixture is stirred at temperatures ranging from 0° to 100° C. until the reaction is judged to be complete. The reaction is worked up by pouring the mixture onto a large excess of water or ice/water and the crude product is either collected by filtration or extracted with ethyl acetate, diethyl ether or other similar solvents. The extracts are concentrated and the compounds, 3, are either purified by crystallization or by flash chromatography. Compounds, 3, are dissolved in an ethereal solvent such as tetrahydrofuran (THF) or diethyl ether, cooled (–78° C.) and treated with an excess of n-butyllithium for such a time to achieve complete dianion formation. The mixture is allowed to warm slightly and sulfur dioxide $SO_2$ is bubbled onto the surface of the reaction until an excess of $SO_2$ has been condensed (acidic to litmus paper). Generally, the mixture is concentrated and water containing sodium acetate is added and cooled to 0° C. Hydroxylamine-O-sulfonic acid is added in excess followed by stirring for 18 h. The mixture is extracted with ethyl acetate, dried and concentrated to give the crude product. Pure 1a is obtained by recrystallization and/or chromatography.

1b is obtained according to Scheme 1c using conditions similar to those described above for Scheme 1a wherein $R_3$ is as previously defined.

Another method for the preparation of 1d is based on the reduction of 4, usually under acidic conditions (Scheme 2). This method furnished directly compounds wherein the $R_2$ substituent is hydrogen.

Scheme 2:

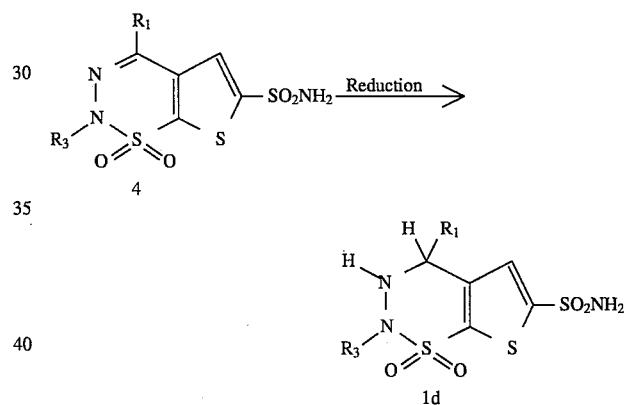

The compounds can be incorporated into various types of ophthalmic formulations for delivery to the eye. These compounds may be combined with ophthalmologically acceptable preservatives, surfactants, viscosity enhancers, penetration enhancers, buffers, sodium chloride, and water to form an aqueous, sterile ophthalmic suspension or solution. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, Carbopol-940 or the like according to the published formulations for analogous ophthalmic preparations; preservatives and tonicity agents can be incorporated. Ophthalmic solution formulations may be prepared by dissolving the active ingredient in a physiologically acceptable isotonic aqueous buffer. Further, the ophthalmic solution may include an ophthalmologically acceptable surfactant to assist in dissolving the active ingredient. A thickener, such as hydroxymethylcellulose, hydroxypropylmethylcellulose, methylcellulose, polyvinylpyrrolidone, or the like, to improve the retention of the medicament in the conjunctival sac.

The compounds are preferably formulated as topical ophthalmic suspensions or solutions, with a pH of about 4.5 to 8.0. The compounds will normally be contained in these formulations in an amount of 0.1% to 10% by weight, but preferably in an amount of 0.25% to 5.0% by weight. Thus, for topical presentation these formulations would be delivered to the surface of a mammal's eye 1 to 4 times a day according to the routine discretion of a skilled clinician.

The following examples, which are in no way limiting, illustrate the preparation of selected examples of the compounds of the present invention. The compound set forth in Example 1 represents the preferred thiophene sulfonamide.

EXAMPLE 1

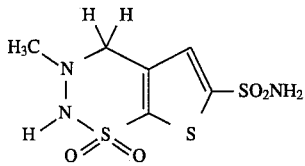

3,4-Dihydro-2H-thieno[3,2-e]-1,2,3-thiadiazine-3-methyl-6-sulfonamide 1,1-dioxide Scheme 1:

Step A. 3-(1,3-Dioxan-2-yl)-2-hydrazinosulfonylthiophene.

To a solution of 3-(1,3-dioxan-2-yl) thiophene (3.6 g, 23 mmol) in dry THF (40 mL) at −78° C. was added dropwise n-butyllithium (2.5M in hexane, 10.15 mL, 25 mmol). After stirring at −78° C. for 1 h, a stream of sulfur dioxide was passed through the surface of the mixture for 15 min. then the mixture was allowed to warm to room temperature. The solvent was evaporated to give a residue which was dried in vacuo. This was dissolved in methylene chloride (60 mL) and cooled to 0° C. N-chlorosuccinimide (3.99 g, 29 mmol) was added. The mixture was allowed to warm to room temperature and stirred for 2 h then the THF was evaporated. The oil obtained was diluted with water (80 mL), extracted with ethyl acetate (3×30 mL), ethyl acetate fractions were combined, dried over $MgSO_4$ and evaporated to give the sulfonyl chloride intermediate as a brown oil. The sulfonyl chloride was dissolved in THF and then added to a cold solution of hydrazine in THF (−10° C.). After 15 min. the mixture was allowed to warm to room temperature and stirred for 2 h. THF was evaporated and the residue obtained was diluted with water (50 mL) and extracted with ethyl acetate (2×50 mL), the combined extracts were washed with brine (100 mL), dried over $MgSO_4$ and evaporated to give a yellow solid (2.5 g, 43%). CI-MS m/e 250 $(M+H)^+$. $^1$H-NMR (DMSO-$d_6$): δ4.30 (4H, m, $2CH_2$); 6.24 (1H, 1s, CH); 7.17 (1H, d, J=5.2 Hz); 7.75 (1H, d, J=5.2 Hz).

Step B. 2H-Thieno[3,2-e]-1,2,3-thiadiazine-1,1-dioxide.

The solid obtained in step A (2.4 g, 48 mmol) was dissolved in acetone (70 mL). p-toluenesulfonic acid (0.20 g, 1 mmol) was added and the mixture was stirred at refluxing temperature (56° C.) for 2 h. The solvent was evaporated, the residue obtained was dissolved in ethyl acetate, washed with saturated aqueous sodium bicarbonate (20 mL) and brine. The ethyl acetate layer was dried over $MgSO_4$ and evaporated to a green solid which was flash chromatographed (silica, hexane-ethyl acetate gradient) to provide a white solid (1.62 g, 90%). mp: 125°–127° C. CI-MS m/e 189 $(M+H)^+$. $^1$H-NMR (DMSO-$d_6$): δ: 7.44 (1H, d, CH, J=5.0 Hz); 7.44 (1H, d, J=5.0 Hz); 8.05 (1H, d, J=5.0 Hz); 8.24 (1H, 1s, CH=N). $^{13}$C-NMR (DMSO, $d_6$): δ125.96, 132.00, 133.64, 136.96, 137.12.

Step C. 3,4-Dihydro-2H-thieno[3,2-e]-1,2,3-thiadiazine 1,1-dioxide.

A solution or suspension of sodium cyanoborohydride (3.96 g, 63.8 mmol) and the material obtained in step B (3.00 g, 15.95) in THF (50 ml) with a few milligrams of Bromocresol green, is stirred trader Nitrogen in a three necked round flask equipped with a dropping funnel. A solution of para-toluenesulfonic acid monohydrate (12.14 g, 63.8 mmol) in THF (40 mL) was added slowly at room temperature in order to maintain pH around 3.5, the pH is indicated by a tan color of the indicator. The sodium salt of para-toluenesulfonic acid precipitated from the solution. The reaction was monitored by TLC. When starting material was consumed the mixture was filtered. The solid obtained was washed with ethyl acetate and the filtrate was concentrated in vacuo using a rotary evaporator. The resulting residue was flash chromatographed to give a white solid, decomposition >150° C. $^1$H-NMR (DMSO-$d_6$): δ: 3.97 (2H, d, $CH_2$); 6.11 (1H, d, NH, J=3.74 Hz); 7.04 (1H, d, J=5.0 Hz); 7.90 (1H, d, J=5.0 Hz); 8.45 (1H, d J=3.58 Hz).

Step D. 3,4-Dihydro-2H-thieno[3,2-e]-1,2,3-thiadiazine-3-methyl-1,1-dioxide.

The product from step C (1.00 g, 5.30 mmol) was dissolved in DMF (10 mL). Sodium carbonate (1.14 g, 10.75 mmol) was added followed by methyl iodide (0.67 mL, 10.75 mmol). The mixture was stirred for 12 h. DMF was evaporated under high vacuum. The residue obtained was diluted with water (10 mL) and the mixture was extracted with ethyl acetate (3×10 mL). The combined extracts were dried over $MgSO_4$ and evaporated to provide a white solid, this was crystallized in ethyl acetate to give 0.25 g (23%). $^1$H-NMR ($CDCl_3$): δ: 2.69 (3H, s, $CH_3$); 3.89 (2H, s, $CH_2$); 8.47 (1H, s, NH exchangeable); 7.07 (1H, d, CH); 7.91 (1 H, d, CH); 8.47 (1H, s, NH exchangeable).

Step E. 3,4-Dihydro-2H-thieno[3,2-e]-1,2,3-thiadiazine-3-methyl-6-sulfonamide 1,1-dioxide.

The product from step D (0.25 g, 1.37 mmol) was dissolved in dry THF (20 mL) and cooled to −78° C. under nitrogen. n-Butyllithium (1.2 mL of a 2.5M solution in hexanes, 3.00 mmol) was added dropwise, the mixture stirred for i h at −78° C. A steam of sulfur dioxide gas was passed through the surface of the mixture for 15 min and then the mixture was allowed to warm to room temperature. Evaporation of the reaction mixture provided a residue which was dissolved in water (50 mL) to which was added sodium acetate trihydrate (0.60 g, 4.10 mmol); this solution was cooled to 0° C. and hydroxylamine-O-sulfonic acid (0.46 g, 4.10 mmol) was added followed by stirring for 18 h. The reaction mixture was extracted with ethyl acetate (2×20 mL). The combined extracts were dried over $MgSO_4$ and concentrated to a crude oil which was purified by flash column chromatography (silica, hexane-ethyl acetate gradient) to give 0.1 g of a white solid (26%) mp: 163–165. $^1$H-NMR (DMSO-$d_6$): δ: 2.68 (3H, s, $CH_3$); 3.88 (2H, s, $CH_2$); 7.50 (1H, s, CH); 8.00 (2H, s, $NH_2$); 8.70 (1H, s, NH exchangeable). Analysis calculated for $C_6H_9N_3O_4S_3$-0.1 ethyl acetate: C, 26.31; H, 3.38; N, 14.38. Found: C, 26.33; H, 3.38; N, 14.34.

EXAMPLE 2

Ophthalmic Suspension

| Ingredient | Concentration (wt %) |
|---|---|
| 3,4-Dihydro-2H-thieno [3,2-e]-1,2,3-thiadiazine-3-methyl-6-sulfonamide 1,1-dioxide. (Compound) | 3.0% |
| Hydroxypropylmethylcellulose | 0.5% |

| Ingredient | Concentration (wt %) |
|---|---|
| Dibasic Sodium Phosphate | 0.2% |
| Disodium Edetate | 0.01% |
| Sodium Chloride | 0.8% |
| Purified Water | q.s |
| Benzalkonium Chloride | 0.01% |
| Polysorbate 80 | 0.1% |
| NaOH/HCl | pH 7.02 |

The Compound (0.09 g), benzalkonium chloride (0.03 g) and, polysorbate 80 (0.15 g) can be mixed together in water (1.23 g) and ball milled for approximately 4 h. A hydroxypropylmethylcellulose vehicle can be prepared by mixing 2% aqueous hydroxypropylmethylcellulose (40 g), sodium chloride (1.28 g), dibasic sodium phosphate (0.32 g), disodium edetate (0.016 g), sodium chloride (1.28 g) and water (35 g) together and the pH adjusted to 7.4 by the addition of 1N HCl (250 μL). A portion of this vehicle (1.5 mL) can be added to the mixture containing the Compound to furnish the desired suspension.

EXAMPLE 3

Ophthalmic Solution

| Ingredient | Concentration (wt %) |
|---|---|
| 3,4-Dihydro-2H-thieno [3,2-e]-1,2,3-thiadiazine-3-methyl-6-sulfonamide 1,1-dioxide. (Compound) | 0.5% |
| Hydroxyethylcellulose | 0.5% |
| Monobasic Sodium Phosphate | 0.13% |
| Dibasic Sodium Phosphate | 0.01% |
| Benzalkonium Chloride | 0.01% |
| Disodium Edetate | 0.01% |
| Purified Water | q.s. |
| NaCl (Osmolality = 282 mOsm) | 0.4% |
| HCl/NaOH | pH 5.0 |

The Compound (0.06 g) and sodium chloride (0.014 g) can be mixed together in water (1.44 g) and the pH of the solution is adjusted to 5.02 by the addition of 1N NaOH (10 μL). The hydroxyethylcellulose vehicle is then prepared by mixing together monobasic sodium phosphate (0.26 g). dibasic sodium phosphate (0.02 g) and disodium edetate (0.02 g) in water (96.7 g). The benzalkonium chloride (2.0 g) and hydroxyethylcellulose are added to the mixture and the pH is adjusted to 5.01 by the addition of 1N HCl (100 μl). A portion of this vehicle (1.5 g) is added to the solution containing the compound and the pH is adjusted to 5.03 by the addition of 1N NaOH (10 μL).

EXAMPLE 4

Ophthalmic Gel

| Ingredient | Concentration (wt %) |
|---|---|
| 3,4-Dihydro-2H-thieno [3,2-e]-1,2,3-thiadiazine-3-methyl-6-sulfonamide 1,1-dioxide. (Compound) | 1.0% |
| Mannitol | 3.6% |
| Benzalkonium Chloride | 0.01% |
| Carbopol | 3.0% |
| HCl/NaOH | pH 5.0 |

| Ingredient | Concentration (wt %) |
|---|---|
| Purified Water | q.s. |

The mannitol (0.18 g), benzalkonium chloride (0.05 mL), Compound (0.1 g) and carbopol (0.15 g) can all be added to water (4.3 mL) and mixed well. The pH can be adjusted to pH 5.0 and purified water (q.s. to 5 mL) can be added and mixed well to form a gel.

EXAMPLE 5

Ophthalmic Suspension

| Ingredient | Concentration (wt %) |
|---|---|
| 3,4-Dihydro-2H-thieno [3,2-e]-1,2,3-thiadiazine-3-methyl-6-sulfonamide 1,1-dioxide. (Compound) | 2.0% |
| Carbomer 934P | 0.5% |
| Sodium Chloride | 0.4% |
| Mannitol | 2.4% |
| Disodium EDTA | 0.01% |
| Polysorbate 80 | 0.05% |
| Benzalkonium Chloride Solution | 0.01% + 5% xs |
| Sodium Hydroxide | q.s. pH = 7.2 |
| Hydrochloric Acid | q.s. pH = 7.2 |
| Water for Injection | q.s. 100% |

The above ingredients can be mixed together using a method similar to the same general procedure described in Example 2 to furnish the ophthalmic suspension.

We claim:

1. A compound having the following structure:

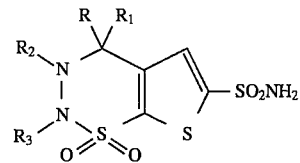

or a pharmaceutically acceptable salt thereof wherein:

R is H or $C_{1-2}$ alkyl;

$R_1$ is H; $C_{1-6}$ alkyl unsubstituted or substituted optionally with OH, $C_{1-4}$ alkoxy, $NR_4R_5$, OC(=O)$R_6$ or C(=O)$R_6$;

$R_2$ is H; $C_{1-6}$ alkyl; $C_{2-4}$ alkyl substituted with OH, $NR_4R_5$, halogen, $C_{1-4}$ alkoxy, $C_{2-4}$ alkoxy$C_{1-4}$ alkoxy, OC(=O)$R_6$, S(=O)$_m R_7$, or C(=O)$R_6$; C(=O)$R_6$;

$R_3$ is H; $C_{1-8}$ alkyl; $C_{1-8}$ alkyl substituted with OH, $NR_4R_5$, halogen, $C_{1-4}$ alkoxy, $C_{2-4}$ alkoxy$C_{1-4}$ alkoxy, OC(=O)$R_6$, S(=O)$_m R_7$, or C(=O)$R_6$; $C_{3-7}$ alkenyl unsubstituted or substituted optionally with OH, $NR_4R_5$, or $C_{1-4}$ alkoxy; $C_{3-7}$ alkynyl unsubstituted or substituted optionally with OH, $NR_4R_5$, or $C_{1-4}$ alkoxy; $C_{0-3}$ alkyl substituted with $R_7$ which can be unsubstituted or substituted optionally with $C_{1-3}$ alkyl, $C_{1-3}$ haloalkyl, OH, $(CH_2)_n NR_4R_5$, halogen, $C_{1-4}$ alkoxy, $C_{1-4}$ haloalkoxy, OC(=O)$R_6$, C(=O)$R_6$, S(=O)$_m R_8$ or $SO_2NR_4R_5$, wherein m is 0–2 and n is 0–2;

$R_4$ and $R_5$ are the same or different and are H; $C_{1-8}$ alkyl; $C_{2-4}$ alkyl substituted optionally with OH, halogen, $C_{1-4}$ alkoxy or C(=O)$R_6$; OH; $C_{1-4}$ alkoxy; $C_{2-4}$ alkoxy substituted optionally with OH, halogen, $C_{1-4}$ alkoxy or C(=O)$R_6$; or $R_4$ and $R_5$ can be joined to form a ring of 5 or 6 atoms selected from O, S, C or N which can be unsubstituted or substituted optionally on carbon with OH, (=O), halogen, $C_{1-4}$ alkoxy, C(=O)$R_6$, $C_{1-6}$ alkyl, $C_{1-6}$ alkyl substituted optionally with OH, halogen, $C_{1-4}$ alkoxy, C(=O)$R_6$ or on nitrogen with $C_{1-4}$ alkyl, C(=O)$R_6$, S(=O)$_m R_8$, $C_{1-6}$ alkyl or $C_{2-6}$ alkyl substituted optionally with OH, halogen, $C_{1-4}$ alkoxy, C(=O)$R_6$ or on sulfur by (=O)$_m$, wherein m is 0–2;

$R_6$ is $C_{1-8}$ alkyl; $C_{1-4}$ alkyl substituted optionally with OH, $NR_4R_5$, halogen, $C_{1-4}$ alkoxy or C(=O)$R_9$; $C_{1-4}$ alkoxy; $C_{2-4}$ alkoxy substituted optionally with OH, $NR_4R_5$, halogen or $C_{1-4}$ alkoxy; or $NR_4R_5$;

$R_7$ is a monocyclic ring system selected from the group consisting of benzene, furan, thiophene, pyrrole, pyrazole, imidazole, triazole, tetrazole, oxazole, isoxazole, isothiazole, thiazole, thiadiazole, pyridine pyrimidine, pyridazine, and pyrazine;

$R_8$ is $C_{1-4}$ alkyl; $C_{2-4}$ alkyl substituted optionally with OH, $NR_4R_5$, $C_{1-4}$ alkoxy or C(=O)$R_6$; $R_7$ which can be unsubstituted or substituted optionally with OH, $(CH_2)_n NR_4R_5$, halogen, $C_{1-4}$ alkoxy, $C_{1-4}$ haloalkoxy, C(=O)$R_6$, S(=O)$_m$ $C_{1-4}$ alkyl or $SO_2NR_4R_5$; wherein m is 0–2 and n is 0–2; and $R_9$ is $C_{1-4}$ alkyl; $C_{1-4}$ alkoxy; amino, $C_{1-3}$ alkylamino, of di-$C_{1-3}$ alkylamino.

2. The compound of claim 1 which is 3,4-Dihydro-2H-thieno[3,2-e]-1,2,3-thiadiazine-3-methyl-6-sulfonamide 1,1-dioxide.

3. A composition for lowering and controlling IOP comprising a pharmaceutically effective amount of a compound having the following structure:

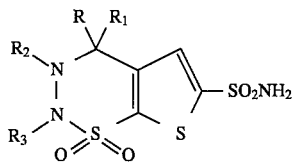

or a pharmaceutically acceptable salt thereof wherein:

R is H or $C_{1-2}$ alkyl;

$R_1$ is H; $C_{1-6}$ alkyl unsubstituted or substituted optionally with OH, $C_{1-4}$ alkoxy, $NR_4R_5$, OC(=O)$R_6$, or C(=O)$R_6$;

$R_2$ is H; $C_{1-6}$ alkyl; $C_{2-4}$ alkyl substituted with OH, $NR_4R_5$, halogen, $C_{1-4}$ alkoxy, $C_{2-4}$ alkoxy$C_{1-4}$ alkoxy, OC(=O)$R_6$, S(=O)$_m R_7$, or C(=O)$R_6$; C(=O)$R_6$;

$R_3$ is H; $C_{1-8}$ alkyl; $C_{1-8}$ alkyl substituted with OH, $NR_4R_5$, halogen, $C_{1-4}$ alkoxy, $C_{2-4}$ alkoxy$C_{1-4}$ alkoxy, OC(=O)$R_6$, S(=O)$_m R_7$, or C(=O)$R_6$; $C_{3-7}$ alkenyl unsubstituted or substituted optionally with OH, $NR_4R_5$, or $C_{1-4}$ alkoxy; $C_{3-7}$ alkynyl unsubstituted or substituted optionally with OH, $NR_4R_5$, or $C_{1-4}$ alkoxy; $C_{0-3}$ alkyl substituted with $R_7$ which can be unsubstituted or substituted optionally with $C_{1-3}$ alkyl, $C_{1-3}$ haloalkyl, OH, $(CH_2)_n NR_4R_5$, halogen, $C_{1-4}$ alkoxy, $C_{1-4}$ haloalkoxy, OC(=O)$R_6$, C(=O)$R_6$, S(=O)$_m R_8$ or $SO_2NR_4R_5$, wherein m is 0–2 and n is 0–2;

$R_4$ and $R_5$ are the same or different and are H; $C_{1-8}$ alkyl; $C_{2-4}$ alkyl substituted optionally with OH, halogen, $C_{1-4}$ alkoxy or C(=O)$R_6$; OH; $C_{1-4}$ alkoxy; $C_{2-4}$ alkoxy substituted optionally with OH, halogen, $C_{1-4}$ alkoxy or C(=O)$R_6$; or $R_4$ and $R_5$ can be joined to form a ring of 5 or 6 atoms selected from O, S, C or N which can be unsubstituted or substituted optionally on carbon with OH, (=O), halogen, $C_{1-4}$ alkoxy, C(=O)$R_6$, $C_{1-6}$ alkyl, $C_{1-6}$ alkyl substituted optionally with OH, halogen, $C_{1-4}$ alkoxy, C(=O)$R_6$ or on nitrogen with $C_{1-4}$ alkyl, C(=O)$R_6$, S(=O)$_m R_8$, $C_{1-6}$ alkyl or $C_{2-6}$ alkyl substituted optionally with OH, halogen, $C_{1-4}$ alkoxy, C(=O)$R_6$ or on sulfur by (=O)$_m$, wherein m is 0–2;

$R_6$ is $C_{1-8}$ alkyl; $C_{1-4}$ alkyl substituted optionally with OH, $NR_4R_5$, halogen, $C_{1-4}$ alkoxy or C(=O)$R_9$; $C_{1-4}$ alkoxy; $C_{2-4}$ alkoxy substituted optionally with OH, $NR_4R_5$, halogen or $C_{1-4}$ alkoxy; or $NR_4R_5$;

$R_7$ is a monocyclic ring system selected from the group consisting of benzene, furan, thiophene, pyrrole, pyrazole, imidazole, triazole, tetrazole, oxazole, isoxazole, isothiazole, thiazole, thiadiazole, pyridine pyrimidine, pyridazine, and pyrazine;

$R_8$ is $C_{1-4}$ alkyl; $C_{2-4}$ alkyl substituted optionally with OH, $NR_4R_5$, $C_{1-4}$ alkoxy or C(=O)$R_6$; $R_7$ which can be unsubstituted or substituted optionally with OH, $(CH_2)_n NR_4R_5$, halogen, $C_{1-4}$ alkoxy, $C_{1-4}$ haloalkoxy, C(=O)$R_6$, S(=O)$_m$ $C_{1-4}$ alkyl or $SO_2NR_4R_5$; wherein m is 0–2 and n is 0–2; and $R_9$ is $C_{1-4}$ alkyl; $C_{1-4}$ alkoxy; amino, $C_{1-3}$ alkylamino, of di-$C_{1-3}$ alkylamino.

4. The composition of claim 3 wherein the compound is 3,4-Dihydro-2H-thieno[3,2-e]-1,2,3-thiadiazine-3-methyl-6-sulfonamide 1,1dioxide.

5. A method for lowering and controlling IOP by administering a pharmaceutically effective amount of a compound having the following structure:

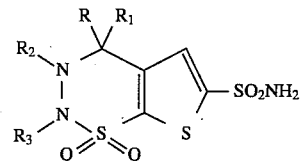

or a pharmaceutically acceptable salt thereof wherein:

R is H or $C_{1-2}$ alkyl;

$R_1$ is H; $C_{1-6}$ alkyl unsubstituted or substituted optionally with OH, $C_{1-4}$ alkoxy, $NR_4R_5$, OC(=O)$R_6$ or C(=O)$R_6$;

$R_2$ is H; $C_{1-6}$ alkyl; $C_{2-4}$ alkyl substituted with OH, $NR_4R_5$, halogen, $C_{1-4}$ alkoxy, $C_{2-4}$ alkoxy$C_{1-4}$ alkoxy, OC(=O)$R_6$, S(=O)$_m R_7$, or C(=O)$R_6$; C(=O)$R_6$;

$R_3$ is H; $C_{1-8}$ alkyl; $C_{1-8}$ alkyl substituted with OH, $NR_4R_5$, halogen, $C_{1-4}$ alkoxy, $C_{2-4}$ alkoxy$C_{1-4}$ alkoxy, OC(=O)$R_6$, S(=O)$_m R_7$, or C(=O)$R_6$; $C_{3-7}$ alkenyl unsubstituted or substituted optionally with OH, $NR_4R_5$, or $C_{1-4}$ alkoxy; $C_{3-7}$ alkynyl unsubstituted or substituted optionally with OH, $NR_4R_5$, or $C_{1-4}$ alkoxy; $C_{0-3}$ alkyl substituted with $R_7$ which can be unsubstituted or substituted optionally with $C_{1-3}$ alkyl, $C_{1-3}$ haloalkyl, OH, $(CH_2)_n NR_4R_5$, halogen, $C_{1-4}$ alkoxy, $C_{1-4}$ haloalkoxy, OC(=O)$R_6$, C(=O)$R_6$, S(=O)$_m R_8$ or $SO_2NR_4R_5$, wherein m is 0–2 and n is 0–2;

$R_4$ and $R_5$ are the same or different and are H; $C_{1-8}$ alkyl; $C_{2-4}$ alkyl substituted optionally with OH, halogen, $C_{1-4}$ alkoxy or C(=O)$R_6$; OH; $C_{1-4}$ alkoxy; $C_{2-4}$ alkoxy substituted optionally with OH, halogen, $C_{1-4}$ alkoxy or C(=O)$R_6$; or $R_4$ and $R_5$ can be joined to form a ring of 5 or 6 atoms selected from O, S, C or N which can be unsubstituted or substituted optionally on carbon with OH, (=O), halogen, $C_{1-4}$ alkoxy, $C(=O)R_6$, $C_{1-6}$ alkyl, $C_{1-6}$ alkyl substituted optionally with OH, halogen, $C_{1-4}$ alkoxy, $C(=O)R_6$ or on nitrogen with $C_{1-4}$ alkoxy, $C(=O)R_6$, $S(=O)_mR_8$, $C_{1-6}$ alkyl or $C_{2-6}$ alkyl substituted optionally with OH, halogen, $C_{1-4}$ alkoxy, $C(=O)R_6$ or on sulfur by $(=O)_m$, wherein m is 0–2;

$R_6$ is $C_{1-8}$ alkyl; $C_{1-4}$ alkyl substituted optionally with OH, $NR_4R_5$, halogen, $C_{1-4}$ alkoxy or $C(=O)R_9$; $C_{1-4}$ alkoxy; $C_{2-4}$ alkoxy substituted optionally with OH, $NR_4R_5$, halogen or $C_{1-4}$ alkoxy; or $NR_4R_5$;

$R_7$ is a monocyclic ring system selected from the group consisting of benzene, furan, thiophene, pyrrole, pyrazole, imidazole, triazole, tetrazole, oxazole, isoxazole, isothiazole, thiazole, thiadiazole, pyridine pyrimidine, pyridazine, and pyrazine;

$R_8$ is $C_{1-4}$ alkyl; $C_{2-4}$ alkyl substituted optionally with OH, $NR_4R_5$, $C_{1-4}$ alkoxy or $C(=O)R_6$; $R_7$ which can be unsubstituted or substituted optionally with OH, $(CH_2)_nNR_4R_5$, halogen, $C_{1-4}$ alkoxy, $C_{1-4}$ haloalkoxy, $C(=O)R_6$, $S(=O)_m$ $C_{1-4}$ alkyl or $SO_2NR_4R_5$; wherein m is 0–2 and n is 0–2; and $R_9$ is $C_{1-4}$ alkyl; $C_{1-4}$ alkoxy; amino, $C_{1-3}$ alkylamino, of di-$C_{1-3}$ alkylamino.

6. The method of claim 5 wherein the compound is 3,4-Dihydro-2H-thieno[3,2-e]-1,2,3-thiadiazine-3-methyl-6-sulfonamide 1,1-dioxide.

* * * * *